United States Patent [19]

Enderby

[11] 4,273,109
[45] Jun. 16, 1981

[54] FIBER OPTIC LIGHT DELIVERY APPARATUS AND MEDICAL INSTRUMENT UTILIZING SAME

[75] Inventor: Charles E. Enderby, Palo Alto, Calif.

[73] Assignee: Cavitron Corporation, New York, N.Y.

[21] Appl. No.: 916,383

[22] Filed: Jun. 16, 1978

Related U.S. Application Data

[63] Continuation of Ser. No. 702,596, Jul. 6, 1976, abandoned, which is a continuation-in-part of Ser. No. 636,139, Nov. 28, 1975, abandoned.

[51] Int. Cl.³ .................. A61N 5/06; A61B 17/32
[52] U.S. Cl. ........................... 128/6; 128/303.1; 350/96.26; 219/121 L; 219/121 LR
[58] Field of Search ............ 128/4, 5, 7, 8, 303.1, 128/303.15, 303.17, 397, 398; 350/96.26, 96.25, 96.24, 96.20, 96.18; 219/121 L, 121 LM, 121 LR

[56] References Cited

U.S. PATENT DOCUMENTS

| | | | |
|---|---|---|---|
| 2,699,770 | 1/1955 | Fourestier et al. | 128/6 |
| 3,043,910 | 7/1962 | Hicks, Jr. | 350/96 BC |
| 3,051,035 | 8/1962 | Root | 350/96.26 |
| 3,051,166 | 8/1962 | Hounanian | 128/4 |
| 3,423,581 | 1/1969 | Baer | 350/96.24 |
| 3,455,625 | 7/1969 | Brumley et al. | 350/96.22 |
| 3,572,325 | 3/1971 | Balell et al. | 128/6 |
| 3,622,743 | 11/1971 | Muncheryan | 128/303.1 |
| 3,643,653 | 2/1972 | Takahashi et al. | 128/6 |
| 3,678,741 | 7/1972 | Burley | 350/96.24 |
| 3,710,798 | 1/1973 | Bredemeir | 219/121 L |
| 3,726,272 | 4/1973 | Fukami et al. | 128/6 |
| 3,756,688 | 9/1973 | Hudson | 350/96 WG |
| 3,768,146 | 10/1923 | Braun | 350/96 R |
| 3,780,295 | 12/1973 | Kapron | 350/96 B |
| 3,790,791 | 2/1974 | Anderson | 350/96.25 |
| 3,808,549 | 4/1974 | Maurer | 350/96 WG |
| 3,832,028 | 8/1974 | Kapron | 350/96 WG |
| 3,834,391 | 9/1974 | Block | 128/303.1 |
| 3,834,803 | 9/1974 | Tsukada | 350/96 BC |
| 3,843,865 | 10/1974 | Nath | 219/121 L |
| 3,846,010 | 11/1974 | Love | 350/96 B |
| 3,858,577 | 1/1975 | Bass et al. | 128/8 |
| 3,880,452 | 4/1975 | Fields | 350/96 C |
| 3,906,221 | 9/1975 | Mercier | 350/96.1 |
| 3,920,980 | 11/1975 | Nath | 219/121 L |

FOREIGN PATENT DOCUMENTS

2326786 12/1973 Fed. Rep. of Germany .............. 128/6
1017354 1/1966 United Kingdom .................. 350/96.18

*Primary Examiner*—Robert W. Michell
*Assistant Examiner*—Arthur S. Rose
*Attorney, Agent, or Firm*—Robert M. Skolnik; William R. Evans

[57] ABSTRACT

Disclosed is a fiber optic fiber transmission line which transmits light a distance from its source and is terminated, at its light delivery end, by a second fiber optic fiber of a larger diameter than the first fiber. An interlocking connector keeps the first and second fiber in positive contact in an efficient light energy transmission relationship. A plurality of second fibers form a set of tips for use in causing light convergence or divergence at the transmission line output.

12 Claims, 7 Drawing Figures

FIBER OPTIC LIGHT DELIVERY APPARATUS AND MEDICAL INSTRUMENT UTILIZING SAME

This is a continuation of pending application Ser. No. 702,596, filed July 6, 1976, now abandoned, which aplication is a continuation-in-part of application Ser. No. 636,139, filed Nov. 28, 1975, copending therewith and now abandoned.

BACKGROUND OF THE INVENTION a. Field of the Invention

The invention relates to fiber optic light energy delivery apparatus and more particularly to an endoscope having a plurality of output tips for selectively converging or diverging light energy.

b. Prior Art

Fiber optic single fiber light energy transmission lines for use in surgical applications are known. For example, U.S. Pat. No. 3,858,577 shows a flexible endoscope with fiber optic fibers transmitting light energy from a laser to a distance output end. The article entitled "Laser-Induced Hemostasis in the Canine Stomach" by Dwyer et al. in JAMA, Feb, 3, 1975, Vol. 231, No. 5, p. 486 describes a surgical application for a flexible fiber optic delivery system.

One of the problems which existed in the past was that blood or other debris would occasionally impinge upon the output aperture of the fiber optic fiber. Often light energy would be absorbed by the blood or debris and cause intense local heating of the fiber, sometimes deforming the fiber at its output aperture. To solve this problem, pieces of glass larger in diameter than the fiber optic fiber have been adhered to the fiber for lowering the energy density of light emerging from the fiber thereby limiting the amount of local heating which can occur in any one place.

Energy density may be lowered in a tapered fiber such as shown in U.S. Pat. No. 3,843,865, but a tapered fiber allows little adjustment of beam spot size once a particular taper is selected. In the aforementioned U.S. Pat. No. 3,858,577 different thicknesses of glass may be placed in front of a fiber output aperture, but in achieving small beam spot sizes, localized heating may occur in the glass and may damage the glass and the fiber.

It is an object of the present invention to devise a means for terminating a fiber optic transmission line which avoids localized heating of the light output region, yet which allows selection of a convergent beam or a divergent beam transmitted from a fiber optic fiber.

SUMMARY OF THE INVENTION

The above object is achieved in a light energy transmission line which includes a fiber optic fiber of a first diameter which transmits light from a light source coupled to an entrance aperture of the fiber through the fiber to its exit aperture at an end of the fiber which is opposite the entrance aperture. This fiber has a first diameter which is generally uniform along the fiber length. The first diameter fiber is coupled to an internally reflecting optical member which has at least an output aperture of greater diameter than the fiber such that light which is transmitted down the first diameter fiber enters the second larger diameter member wherein the energy density is spread out, yet the beam characteristic of the light transmitted down the fiber is preserved and light energy is conserved because of the nearly total internal reflection of the second fiber. Preferably the member is short and another fiber.

The two fibers are mechanically joined by an interlocking connector having first and second interlocking sleeves which are mutually coaxially affixed to each of the two fibers proximate the regions where they abut. The two fibers are optically joined so that reflection of light at the boundary of the two fibers is minimized. A plurality of second fibers can also be provided forming a set of interchangeable output tips. Each output tip comprises an internally reflecting optical member, such as a short fiber optic fiber, having an input aperture optically coupled to the exit aperture of the longer fiber optic fiber, said coupling being an efficient light energy transmission relationship. The greater diameter of the other fiber spreads out the energy density transmitted along the length of the long fiber. The exit apertures of the set of tips can have a different curvature in each tip such that a desired tip may be selected for adjusting beam spot size and for selecting a converging or a diverging beam.

The new fiber optic transmission line with a selected output tip may be utilized in a medical instrument of the type having elongated chambers therein for entry of light, such as a cystopscope or an endoscope. The fiber optic transmission line is inserted in one of the open chambers of such an instrument after being enclosed in a sheath which is coaxial with the long first diameter fiber for keeping the fiber from contacting the interior boundaries of the length of the elongated chamber, while at the same time preserving space between the fiber itself and the walls of the sheath, thereby preserving the internal reflection characteristic of the fiber optic fiber transmission line.

The invention will be more clearly understood with reference to the following drawings.

DESCRIPTION OF THE PREFERRED EMBODIMENT

Figure 1:
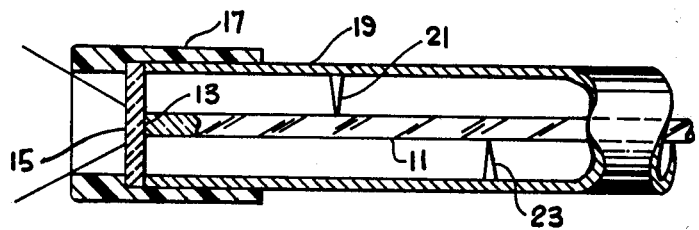
FIG. 1 shows a side partial cutaway view of the output end of a fiber optic light delivery apparatus of the prior art.

FIG. 1 shows a prior art fiber optic fiber 11 transmitting light from an input aperture, not shown, to an output end 13. To prevent localized heating on output end 13 a piece of glass 15 which has a larger diameter than the output end 13 is secured to the fiber 13 by means of an end cap 17 which typically has a friction fit sleeve 19 which is either in direct contact with fiber 11 or is spaced therefrom by means of spacers 21, 23. The approximate outside diameter of the sleeve 19 in prior art apparatus has been slightly less than 5 millimeters. One of the problems of this prior art apparatus is not only the problem of beam divergence previously described, but also the fact that the cap 17, being held by a friction fit, may be pulled off of sleeve 19 if the cap becomes lodged in a narrow space. On the other hand, if cap 17 is cemented in place, it is difficult to remove glass 15 for cleaning or for changing the optical properties of the glass.

Figure 2:
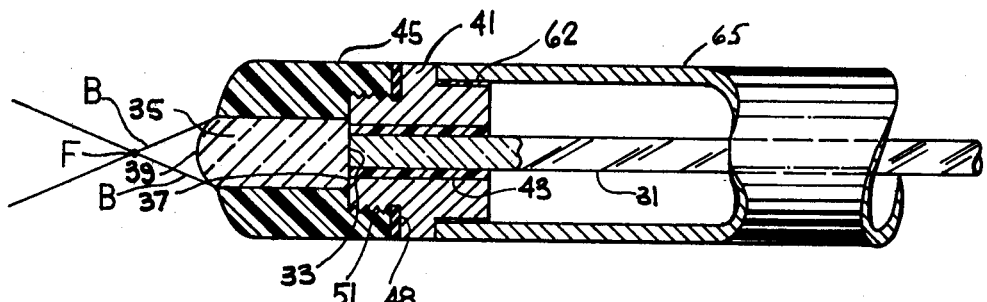
FIG. 2 shows a side partial cutaway view of an output tip with a convex face of a fiber optic fiber light delivery apparatus of the present invention, taken along the line 2—2 in FIG. 4.

In FIG. 2, the side sectional view of the present invention is seen wherein an elongated fiber optic fiber 31 has an entrance aperture not shown at a first end fiber, which is coupled to a light source, such as a laser. Fiber 31 has a generally uniform diameter along its length of approximately 100 microns. This diameter is illustrative of the diameter for the fiber to be used to transmit laser light for medical applications, although larger or smaller fibers may be used, depending on the application. A 100 micron fiber is suitable for delivering output power from an argon ion laser. Fiber 31 has an exit aperture 33 which is preferably a flat polished surface.

Figure 3:
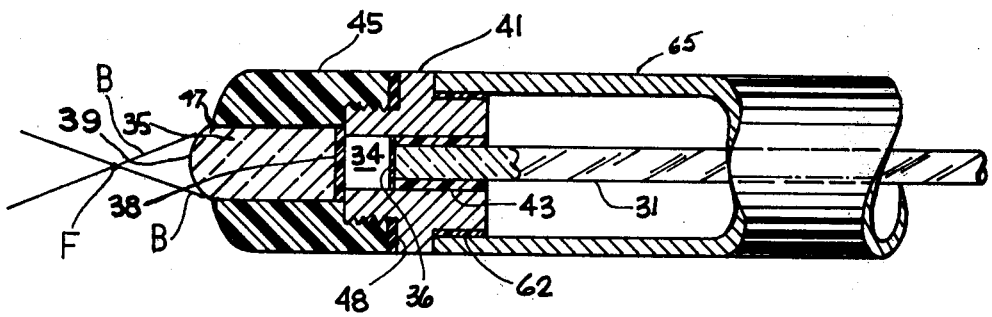
FIG. 3 shows an alternate construction of the apparatus of FIG. 2.

A fiber optic fiber 35 having a second diameter, greater in diameter than the first diameter and axially aligned therewith, and usually having an index of refraction identical with first diameter fiber 31 forms a portion of an output tip for fiber 31. Fiber tip 35 has an input aperture 37 which abuts the exit aperture of the first diameter fiber 31. The diameter of the second diameter fiber 35 is approximately 0.5 millimeters and is generally of uniform diameter along the length of the fiber. The input aperture 37 of the second diameter fiber 35 has a surface which is congruent with the surface of the exit aperture 33 of the first diameter fiber 31. By congruent surfaces, it is meant that the two surfaces couple light energy between themselves with a high degree of efficiency. This may be achieved by polishing fiber ends which face each other and then bringing them into abutting contact. Another means of coupling light energy between the two fibers with a high degree of efficiency is by applying a coating to each fiber face of a type which will couple light efficiently to an intervening medium, as illustrated in FIG. 3.

For example, if the intervening material is air 34 between the two fibers, one fiber is coated with a first coating 36 which couples light energy in the first fiber 31 to air 34 and the second fiber 35 is coated with a second coating 38 which couples the light energy from the air 34 to the second fiber 35. The intervening medium need not be a gas such as air, such may be a liquid or a solid, but as a piece of quartz, glass or plastic which can transfer light energy efficiently. Coupling of light energy to an intervening medium is useful where the first diameter fiber has an index of refraction different from the second diameter fiber. Coatings may be used to couple light energy between the two through the intervening medium, as described.

The second diameter fiber 35 has an output aperture 39 opposite the input aperture 37. The output aperture 39 may have the characteristics of a lens, such as curvature which will cause convergence of a beam, discussed above. Fiber tip 35 may be a focusing fiber i.e. a fiber having the characteristic of focusing light at a desired focal length. Such a focusing fiber has a convex face 39.

One of the advantages of the present invention is that the second diameter fiber 35 may be removed and replaced by another fiber output tip having different optical properties, such as focal length or beam convergence or divergence characteristics. For example, in certain medical applications it may be desirable to have a divergent beam for cauterization of a large area, or on the other hand, it may be desirable to have a rather narrow diameter beam for cauterizing a blood vessel or other small site. Other output tips will be described with reference to FIGS. 6 and 7 below.

The apparatus of the present invention utilizes an interlocking connector having a pair of interlocking sleeves for the purpose of allowing interconnection of various output tips. In FIG. 3 a first connector sleeve 41 is coaxially affixed to first diameter fiber 31 by an adhesive such as the epoxy layer 43. The first sleeve is affixed to the first fiber proximate the end where the exit aperture resides. A second connector sleeve 45 is coaxially affixed, such as by an adhesive layer 47, for example epoxy, to the second diameter fiber 35 or the fiber 35 may be affixed to sleeve 45 by a tight friction fit if sleeve 45 is made of plastic. If sleeve 45 is made of metal, epoxy should be used. The connector must reside at least proximate to the input aperture 37 of the second fiber 35 so that when the connector sleeves 41, 45 are joined, exit aperture 33 and input aperture 37 may be brought into abutting contact.

It will be seen that connector sleeve 45 extends along the entire length of the second diameter fiber 35 and serves as a protective cover or cap for that fiber. The first sleeve 41 has threads 51 along an interior sleeve portion while the sleeve 45 has matching threads along an interior sleeve portion. Matching threads are threads of approximately the same pitch and diameter which allow one sleeve to be screwed onto the other with a relatively tight fit therebetween with a gasket 48 sealing the space between sleeves. While gasket 48 is shown to be an annular type seal, portions of sleeves 41 and 45 may be various type of seals, so that seal segments form a means for interlocking fiber 31 to fiber 35. In the simplest configuration of the invention a fiber optic fiber 31 of a first diameter is interlocked by means of a seal with a fiber optic fiber 35 of a second diameter, greater than the first diameter, wherein the seal permits transmission of light energy from fiber 31 to fiber 35. The simplest seal need not be a mechanical seal, but may be a chemical seal.

In many applications, the first diameter fiber 31 is a relatively long fiber, perhaps two meters or more whereas the second diameter fiber 35 is relatively short, approximately five or six millimeters. It can be seen that several second diameter fibers 35 may be provided with sleeves 45 of a diameter and pitch which will match the threads of sleeve 41 whereby the second connector sleeves may each have separate desired optical characteristics obtained from a second diameter fiber 35 enclosed therein.

In many uses, it is desirable to provide a sheath 65 for the first diameter fiber 31 along its entire length in order to protect the fiber from coming into contact with foreign objects. If foreign objects come into contact with fiber 31 the fiber may lose some of its properties of total internal reflection.

In the prior art, it has been the practice to provide a sheath which is spaced by means of spacers from the fiber. However, even spacers of the prior art can cause a slight loss of total internal reflection.

In the present apparatus, a glass cladding is provided about the fiber with the index of refraction of the cladding less than the index of refraction for the fiber thereby providing total internal reflection in the fiber.

Such fibers may be purchased commercially. A protective sheath 65 has an outside diameter approximately 2 millimeters and is preferably a silk woven catheter, having the property that no kinks will form when the sheath is twisted and will not stretch, thereby protecting the fiber. The sheath 65 is affixed to sleeve 41 at one end by means of an annular epoxy coating 62 and to another sleeve, not shown, at the distal end of fiber 31.

Figure 4:
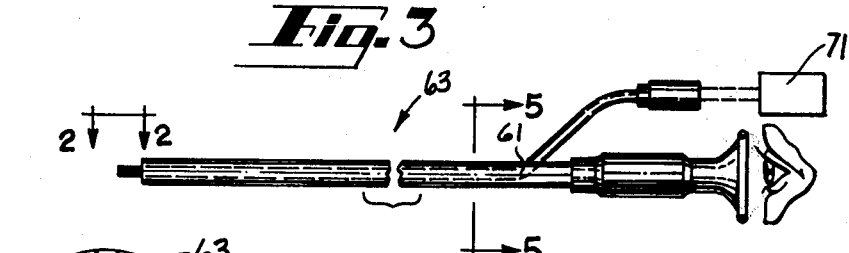
FIG. 4 is a plan view of a medical instrument utilizing the apparatus of the present invention.
Figure 5:
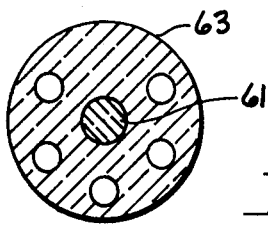
FIG. 5 is a cross-sectional of the medical instrument of FIG. 4, taken along lines 5—5.

With reference to FIGS. 4 and 5, the apparatus thus described may be used in one of the elongated chambers 61 of the medical instrument 63 of the type for delivering light energy from a source 71, such as a laser, to an internal organ or tissue of the human body. These instruments are generally known as endoscopes and include cystoscopes, vocal chord fiberscopes, broncofiberscopes, esophagofiberscopes, dudenofiberscopes, choledochofiberscopes, colonofiberscopes, and gastrofiberscopes, illustrated generally in FIG. 4 and in section in FIG. 5, although details of each instrument may vary slightly. The apparatus may be used to deliver light either for illumination or cauterizing as previously described. In such applications, the fiber optic light transmission line 31 of the present invention may be withdrawn from the instrument and a different second sleeve 45 enclosing an optically different second diameter fiber 35 may be quickly changed for different purposes during the same medical procedure. The positive interlocking connection between threads keeps the second diameter fiber 35 in abutting contact with the first fiber 31 during the entirety of its use, until the interlocking connection is removed.

In FIGS. 2 and 3, it will be seen that the output tip is convex for focusing the beam B—B at point F. The amount of curvature provided to output aperture 39 determines the position of focal point F in accord with known principles of geometrical optics. This curvature controls beam spot size at distances from output aperture 39 and hence, beam output energy at a target location surgical cutting may be done with fine beam sizes, while cauterization is usually performed with larger spot sizes.

Figure 6:
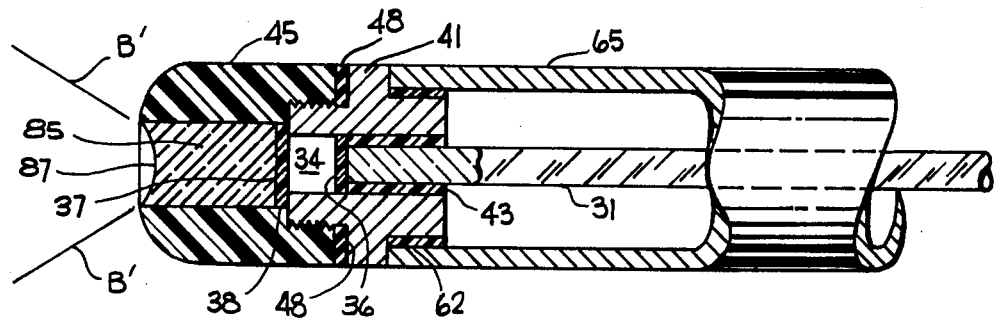
FIG. 6 shows a side partial cutaway view of an output tip with a concave face of a fiber optic fiber light delivery apparatus.

FIG. 6 corresponds generally to FIG. 3, except that the second fiber 85 has a concave output aperture 87 for creating a divergent beam, B—B. The degree to which output aperture 87 is made concave depends on the amount of angular beam divergence desired, in accord with well known principles of geometrical optics.

The second fiber 85 has a second diameter, greater in diameter than the diameter of first fiber 31 and axially aligned therewith, and usually has an index of refraction identical with the first diameter fiber. The second fiber 85 forms a portion of an output tip for the first fiber 31. The second fiber 85 has an input aperture 37 which is coupled to the exit aperture of the first diameter fiber. For example, such coupling of light energy may be through an air space 34. In such a case the first fiber 31 is coated with a first coating 36 which couples light energy in the first fiber of 31 to air 34 and the second fiber 85 is coated with a second coating 38 which couples light energy from the air space 34 to the second fiber 85. As mentioned previously the intervening medium need not be air but may be a liquid or a solid through which light energy can be efficiently transferred. Coupling by means of coatings is an alternative to the construction of FIG. 2 wherein the first and second fibers are brought into abutting contact. The two fibers of FIG. 6 could be brought into contact in the same manner as the two fibers of FIG. 2 as long as the exit aperture of the first fiber 31 has a congruent surface with the input aperture 37 of the second fiber and the input aperture of the second fiber is at least as great in diameter as the output aperture of the first fiber.

Figure 7:
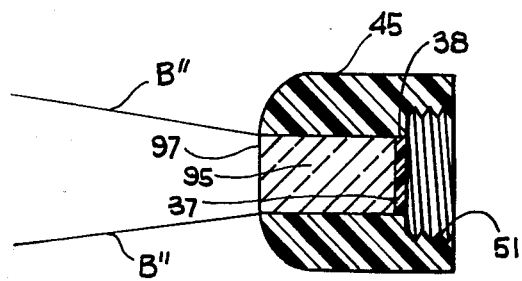
FIG. 7 shows a side view of an output tip with a flat face of a fiber optic fiber light delivery apparatus of the present invention.

FIG. 7 shows still another output tip for a medical instrument in which a second fiber 95 has a plane output aperture generating a slightly divergent beam B"—B". The second fiber 95 is coaxially surrounded by a connector sleeve 45 having internal threads 51. A coating 38 may be applied to the input aperture 37 of fiber 95 so that fiber 95 may be optically coupled to a first fiber 31 when the output tip is screwed for a first connector sleeve 41 of a medical instrument or the like.

By providing a plurality of output tips such that convergent and divergent beams may be selected, a greater degree of versatility is provided in medical instruments utilizing a single fiber optic fiber for transmission of light energy.

While certain dimensions have been given in characterizing the invention, these dimensions are not critical and other dimensions, smaller or larger, may be used. Moreover, the usefulness of the fiber optic light transmission invention is not restricted to medical instruments, but may be used in industrial applications.

I claim:

1. In a light energy delivery apparatus having an elongated fiber optic fiber having along its length a first transverse crossectional diameter, an entrance aperture at a first end of said fiber and an exit aperture at a second end of said fiber opposite said entrance aperture, a high energy light source mounted adjacent said entrance aperture such that when energized said light source directs light into said first end of said fiber, the improvement of output optics comprising, an internally reflecting optical member having input aperture means for receiving light from said exit aperture of said optic fiber and output aperture means for discharging light, the length of said optical member between said output and input apertures being longer than the width of said optical member, said optical member having a second transverse crossectional diameter greater substantially all along its length than said first transverse crossectional diameter of said fiber, and connecting and coupling means for releasably interlocking said input aperture means of said optical member to said exit aperture of said fiber and optically coupling the same in an efficient light energy-transmissive relation.

2. The apparatus of claim 1 wherein said output aperture means of said internally reflecting optical member has a convex face curvature.

3. The apparatus of claim 1 wherein said output aperture means of said internally reflecting optical member has a concave face curvature.

4. The apparatus of claim 1 wherein said output aperture means of said internally reflecting optical member has a planer face.

5. The apparatus of claim 1 wherein said internally reflecting optical member has a face on said output aperture with a focal length of less than one inch.

6. The apparatus of claim 1 further comprising in combination said fiber optic fiber of said first diameter.

7. The apparatus of claim 6 wherein said connecting and coupling means comprises a first connector sleeve coaxially affixed to said fiber at least proximate to its exit aperture means and a second connector sleeve coaxially affixed to said internally reflecting optical member at least proximate to its input aperture means and means on each sleeve for interlocking them and releasing them only when desired.

8. The apparatus of claim 7 further comprising a plurality of said second connector sleeves, each for interchangeably interlocking with said first connector sleeve and each being coaxially affixed to one of a corresponding plurality of said internally reflecting optical members, said output aperture means of each said internally reflecting optical member having different optical properties.

9. The apparatus of claim 1 wherein said internally reflecting optical member is another fiber optic fiber.

10. The apparatus of claim 9 wherein said other fiber optic fiber is cylindrical between said input and output aperture means.

11. The apparatus of claim 1, and further comprising a plurality of said internally reflecting optical members each having said output aperture means with a different optical property whereby to form a set of members for interchangeably interlocking with said fiber.

12. An endoscope comprising,
   a first elongated fiber optic fiber enclosed in a coaxial sheath and having along its length a first transverse crossectional diameter, entrance aperture means at a first end of said fiber for receiving light, and exit aperture means at a second end of said fiber opposite said entrance aperture for dischanging light, a high energy light source mounted adjacent said entrance aperture such that when energized said light source directs light into said first end of said fiber,
   a second fiber optic fiber of a second transverse crossectional diameter which is greater substantially all along said second fiber optic fiber than said first diameter of said first fiber, and having light input aperture means at a first end thereof for receiving light from the exit aperture means of said first fiber, and output aperture means at a second end opposite said entrance aperture for discharging light, the length of said optical member between said output and input apertures being longer than the width of said optical member, and
   means connected respectively to said second end of said first fiber and said first end of said second fiber of said second diameter for releasably interlocking the exit aperture means of said first fiber and the input aperture means of said second fiber in an efficient light-energy transmissive relation.

* * * * *